United States Patent [19]

Ikezaki et al.

[11] 4,131,686
[45] Dec. 26, 1978

[54] NOVEL BENZYLALCOHOL DERIVATIVES AND PROCESSES FOR PREPARING THE SAME

[75] Inventors: Muneyoshi Ikezaki, Ageo; Yashushi Okazaki, Tokyo; Nobuo Ito, Tokyo; Masao Hoshiyama, Tokyo; Taku Nagao, Ageo; Hiromichi Nakajima, Yono, all of Japan

[73] Assignee: Tanabe Seiyaku Co., Ltd., Osaka, Japan

[21] Appl. No.: 747,898

[22] Filed: Dec. 6, 1976

[30] Foreign Application Priority Data

Dec. 11, 1975 [JP] Japan .................................. 50/148145
Feb. 12, 1976 [JP] Japan .................................. 51/14668

[51] Int. Cl.$^2$ ...................... A61K 31/135; C07C 91/34
[52] U.S. Cl. .................................... 424/330; 260/570.6
[58] Field of Search ....................... 424/330; 260/570.6

[56] References Cited

U.S. PATENT DOCUMENTS

| | | | |
|---|---|---|---|
| 3,139,441 | 6/1964 | Biel | 260/340.5 |
| 3,869,474 | 3/1975 | Miura et al. | 260/343.7 |
| 3,952,021 | 4/1976 | Ikezaki et al. | 260/343.7 |
| 4,032,575 | 6/1977 | Ikezaki et al. | 260/570.6 |

Primary Examiner—Frederick E. Waddell
Attorney, Agent, or Firm—Bierman & Bierman

[57] ABSTRACT

A compound of the formula:

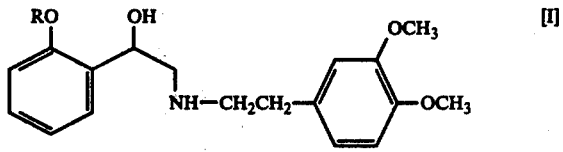

wherein R is lower alkyl, may be prepared, for example, by reducing a compound of the formula:

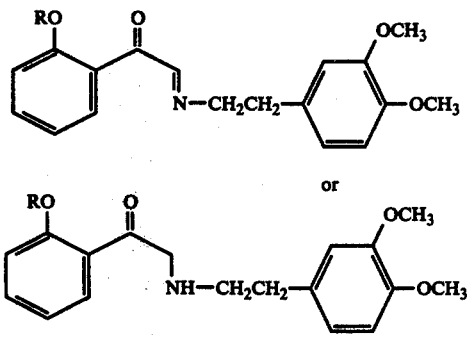

wherein R is same as above. Other methods for preparing the compound [I] are also disclosed. The compound [I] and a pharmaceutically acceptable acid addition salt thereof are useful as anti-diabetic agents.

8 Claims, No Drawings

NOVEL BENZYLALCOHOL DERIVATIVES AND PROCESSES FOR PREPARING THE SAME

This invention relates to a novel benzylalcohol derivative and processes for preparing the same. More particularly, it relates to a racemic mixture or an optically active α-(3,4-dimethoxyphenylethylaminomethyl)-2-alkoxybenzylalcohol, of the formula:

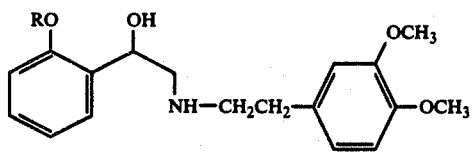

wherein R is lower alkyl, and a pharmaceutically acceptable acid addition salt thereof.

It is known that α-(3,4,5-trimethoxyphenethylaminomethyl)-3,4-dihydroxybenzylalcohol and α-(3,4-dimethoxyphenethylaminomethyl)-3,4-dihydroxybenzylalcohol are prepared by hydrogenating the corresponding 3,4-dibenzyloxybenzylalcohol or 3,4-dibenzyloxyacetophenone in the presence of a catalyst such as palladium-carbon (U.S. Pat. 3869474 and Offenlegungsschrift 2420427). These compounds show selective activation of adrenergic $\beta_1$-receptor and are useful as cardiotonic agents having no substantial influence upon blood-pressure.

We have now found that the benzylalcohol derivative [I] can induce remarkable decrease of blood sugar and is useful as an anti-diabetic agent. The blood sugar-lowering activity of the benzylalcohol derivative [I] is about 3 to 100 times stronger than that of Phenformin (Chemical name: 1-phenethylbiguanide). For example, when dl-α-(3,4-dimethoxyphenethylaminomethyl)-2-methoxybenzylalcohol (Dose: 2 mg/kg) or its l-isomer (Dose: one mg/kg) is administered orally to mice prior to subcutaneous injection of glucose (one g/kg), said 2-methoxybenzylalcohol derivative of the invention decreases the blood sugar level by about 26 to 31%. On the other hand, when examined under the same conditions as above, 100 mg/kg of Phenformin are required to induce about a 30% decrease in the blood sugar. Further, the toxicity of the benzylalcohol derivative [I] is low. For example, the 50% lethal dose ($LD_{50}$) of dl-α-(3,4-dimethoxyphenethylaminomethyl)-2-methoxybenzylalcohol which is estimated by oral administration thereof to mice is about 580 mg/kg.

The benzylalcohol derivative [I] of the present invention can be used for pharmaceutical use either in the form of a racemic mixture or in an optically active form. The benzylalcohol derivative [I] can also be used for pharmaceutical use as the free base or a salt thereof. The base and salt thereof are readily convertible from one to the other by conventional methods. Examples of the pharmaceutically acceptable acid addition salts include inorganic acid addition salts such as hydrochloride, phosphate, nitrate and sulfate, and organic acid addition salts such as acetate, lactate, citrate, tartrate, fumarate, maleate, aspartate, methanesulfonate, benzoate and glycine salt. The benzylalcohol derivative [I] may be administered either orally or parenterally, and may be further used in conjunction or admixture with a pharmaceutical excipient which is suitable for oral or parenteral administration. The pharmaceutical preparation may be a solid dosage form such as pulvers, tablets and capsules, or a liquid dosage form such as a solution, an emulsion or a suspension. A suitable daily dose for oral administration of the derivative [I] may be about 5 μg to 10 mg, especially 20 μg to 2 mg, per kg of body weight.

According to the present invention, the benzylalcohol derivative [I] can be prepared by the steps of:

(i) condensing 3,4-dimethoxyphenethylamine with a phenylglyoxal derivative of the formula:

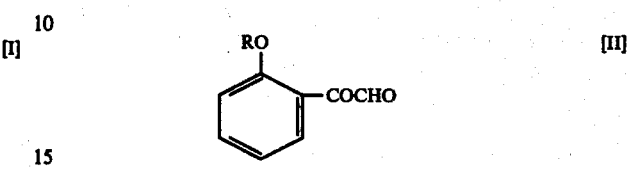

wherein R is the same as defined above, or a hydrate thereof to give an α-(3,4-dimethoxyphenethylimino)acetophenone derivative of the formula:

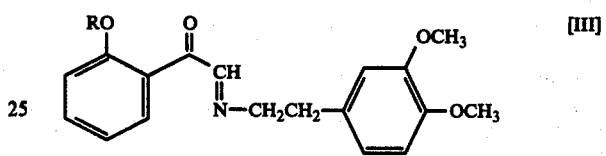

wherein R is the same as defined above, or (ii) condensing 3,4-dimethoxyphenethylamine with an α-(halogenomethyl)acetophenone derivative of the formula:

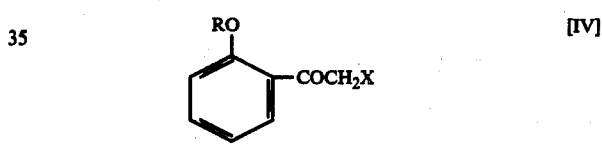

wherein X is halogen and R is the same as defined above, to give an α-(3,4-dimethoxyphenethylamino)acetophenone derivative of the formula:

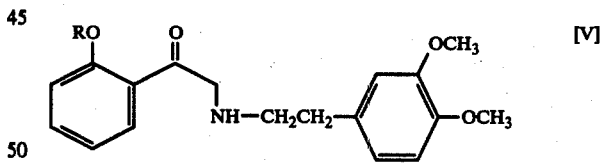

wherein R is the same as defined above, and then (iii) reducing the acetophenone derivative [III] or [V]. The benzylalcohol derivative [I] can also be prepared by condensing 3,4-dimethoxyphenethylamine with an α-(halogenomethyl)benzylalcohol derivative of the formula:

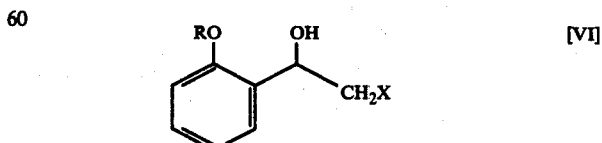

wherein R and X are the same as defined above, or with a 2-phenyloxirane derivative of the formula:

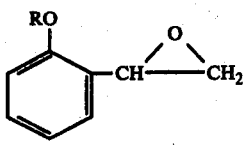

wherein R is the same as defined above. Alternatively, the derivative [I] may be prepared by condensation of N-(3,4-dimethoxyphenethyl)glycine with a phenylaldehyde derivative of the formula:

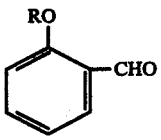

wherein R is the same as defined above.

Each of the starting compounds [II], [IV], [VI] and [VII] is readily obtainable. For example, the compound [II] is obtained by oxidation of a 2-lower alkoxyacetophenone with selenium dioxide according to known methods [e.g., Chemical Abstracts Vol. 66, 46399c (1967); ibid. Vol. 72, 89963Y (1970)]. The starting compound [IV] may be prepared by dropwise addition of sulfuryl halide (e.g., sulfuryl chloride) to a methylene chloride solution of a 2-lower alkoxy-acetophenone at 0° to 30° C. under stirring. Treatment of the compound [IV] with sodium borohydride at 5° to 30° C. in a solvent (e.g., dioxane) gives the compound [VI]. Further, the oxirane derivative [VII] may be prepared from the compound [VI] by treating it with an alkali metal hydroxide (e.g., sodium hydroxide, potassium hydroxide) at room temperature in a solvent (e.g., dioxane).

The condensation of 3,4-dimethoxyphenethylamine with the phenylglyoxal derivative [II] or a hydrate thereof can be accomplished by conventional methods. For example, the compound [III] is prepared by admixing said starting compounds in the presence or absence of a catalyst in a solvent. It is preferred to carry out the reaction at a temperature of 0° to 50° C. Preferred examples of the reaction solvent include dimethylsulfoxide and lower alkanols (e.g., methanol, ethanol). p-Toluenesulfonic acid is suitable as the catalyst. The α-(3,4-dimethoxyphenethylimino)acetophenone derivative [III] thus obtained may be used in the subsequent reaction without isolating it from the reaction solution.

On the other hand, the condensation of 3,4-dimethoxyphenethylamine with the α-(halogenomethyl)acetophenone derivative [IV] is conducted by admixing them in the presence or absence of an acid acceptor. This condensation reaction is preferably carried out at a temperature of 0° to 50° C. Said reaction is also carried out with or without a solvent. Preferred examples of the reaction solvent include methylene chloride, chloroform, dimethylformamide, tetrahydrofuran and a lower alkanol (e.g., methanol, ethanol). Alkali metal hydroxides (e.g., sodium hydroxide, potassium hydroxide), alkali metal carbonates (e.g., sodium carbonate) and organic tertiary amines (e.g., trimethylamine, triethylamine, pyridine) are suitable as the acid acceptor.

The benzylalcohol derivative [I] is prepared by treating the resultant product [III] or [V] with a reducing agent in a solvent. Suitable examples of the reducing agent include an alkali metal borohydride (e.g., sodium borohydride, potassium borohydride, lithium borohydride), lithium aluminum hydride, diborane and aluminium hydride. Lower alkanols (e.g., methanol, ethanol, propanol), aqueous alkanols, tetrahydrofuran, dioxane and the like are suitable as the reaction solvent. It is preferred to carry out the reaction at a temperature of −10° to 30° C. The catalytic hydrogenation of the compound [III] or [V] in the presence of palladium charcoal or platinum dioxide also gives the benzylalcohol derivative [I].

The condensation reaction of 3,4-dimethoxyphenethylamine with the α-(halogenomethyl)benzylalcohol derivative [VI] or the 2-phenyloxirane derivative [VII] is readily conducted by heating a mixture of these compounds. It is preferred to carry out the reaction at a temperature of 50° to 150° C. When the α-(halogenomethyl)benzylalcohol derivative [VI] is employed as the starting compound, the reaction may be carried out either in the presence or absence of an acid acceptor. Suitable examples of said acid acceptor include alkali metal hydroxides (e.g., sodium hydroxide, potassium hydroxide), alkali metal carbonate (e.g., sodium carbonate) and organic tertiary amines (e.g., trimethylamine, triethylamine, pyridine).

Further, the condensation of N-(3,4-dimethoxyphenethyl) glycine with the phenylaldehyde derivative [VIII] is carried out in the presence of an alkali reagent in a solvent. Preferred examples of the alkali reagent include pyridine, triethylamine and Triton-B. It is preferred to carry out the reaction at a temperature of 50° to 150° C. Pyridine and xylene may be suitable as the reaction solvent.

The benzylalcohol derivative [I] thus obtained always exists in the form of a racemic mixture and may be, if required, resolved into each of its optically active enantiomers. The optical resolution of the benzylalcohol derivative [I] into each of its optically active enantiomers may be conducted by reacting the racemic mixture with a resolving agent in a solvent to form the diastereoisomeric salts thereof, and separating said diasteoisomers into each components thereof by selective crystallization. By said selective crystallization, the least soluble diastereoisomer is recovered as crystals from the reaction mixture and the more soluble diastereoisomer remains in the reaction mixture. It is preferred to carry out the selective crystallization at a temperature of −20° to 20° C. Derivatives of optically active tartaric acid (e.g., optically active enantiomers of dibenzoyltartaric acid, diacetyltartaric acid and monobenzoyltartaric acid), d-camphorsulfonic acid, d-α-bromocamphorsulfonic acid, L-(-)-malic acid, l-mandelic acid, quinic acid and optically active amino acid or their derivatives (e.g., optically active enantiomers of N-acetylphenylalanine, glutamic acid and N-carbobenzyloxyglutamic acid) may be used as the resolving agent. The solvent which is employed in this resolution procedure should be the one in which the solubilities of the two diastereoisomers are sufficiently different from each other. For this purpose it is suitable to use water, lower alkanols (e.g., methanol, ethanol), ethyl acetate, chloroform, dimethylformamide or a mixture of these solvents.

Practical and presently-preferred embodiments of the present invention are illustratively shown in the following Examples. Throughout the specification and claims, the term "lower alkyl" should be interpreted as referring to an alkyl group having one to four carbon atoms.

EXAMPLE 1

(1) 3 g of 2-methoxyacetophenone are dissolved in 15 ml of dioxane, and a solution of 3.3 g of selenium dioxide in 1.5 ml of water is added thereto. The solution is refluxed for 15 hours. After the reaction, insoluble materials are removed by filtration, and the filtrate is concentrated. The oily residue thus obtained is dissolved in ethyl acetate. The ethyl acetate solution is washed with water and then with an aqueous sodium bicarbonate solution and water. Then, said solution is dried and evaporated to remove solvent. 3.1 g of 2-methoxyphenylglyoxal hydrate are obtained as a crude oil.

(2) 3.6 g of 3,4-dimethoxyphenethylamine are added to 10 ml of a dimethylsulfoxide solution containing 3.1 g of 2-methoxyphenylglyoxal hydrate (crude oil). The solution is stirred at room temperature for one hour, whereby a solution containing α-(3,4-dimethoxyphenethylimino)-2-methoxyacetophenone is obtained.

(3) 10 ml of methanol are added to the α-(3,4-dimethoxyphenethylimino)-2-methoxyacetophenone solution obtained in paragraph (2). After ice-cooling, 1.5 g of sodium borohydride are added gradually to the solution, and the mixture is stirred at the same temperature for 30 minutes and at room temperature for 2 hours. The reaction mixture is poured into ice-water. The aqueous mixture is extracted with ethyl acetate. The extract is washed with water, dried and then evaporated to remove solvent. The oily residue thus obtained is treated with hydrochloric acid and recrystallized from a mixture of ethanol and ether. 3.2 g of α-(3,4-dimethoxyphenethylaminomethyl)-2-methoxybenzylalcohol hydrochloride are obtained. M.p. 142°–143° C.

Analysis calculated for $C_{19}H_{25}O_4N.HCl$
C, 62.03; H, 7.12; N, 3.81; Cl, 9.64
Found C, 62.19; H, 7.11; N, 3.87; Cl, 9.84

Free Base:
M.p. 92° C. (recrystallized from ethyl acetate)
NMR spectrum:

$\delta CDCl_3$: 2.5 – 3.2(8H), 3.81(3H, S), 3.86(6H, S),
5.12 (1H multiplet), 6.7 – 7.6 (7H Arom)

Mass analysis:
m/e: 332(M + 1)+, 331(M+), 313, 194, 180, 165, 162

EXAMPLE 2

(1) 4.55 g of 2-methoxy-α-chloroacetophenone are dissolved in 70 ml of dioxane, and 30 ml of water are added thereto. 1.5 g of sodium borohydride are added gradually to the solution at 10° to 20° C. Then, the mixture is stirred at room temperature for 3 hours. The reaction mixture is poured into ice-water. The aqueous mixture is extracted with benzene. Then, the extract is dried and evaporated to remove solvent. 3.7 g of α-chloromethyl-2-methoxybenzylalcohol are obtained as a crude oil.

(2) A mixture of 3.7 g of α-chloromethyl-2-methoxybenzylalcohol (crude oil) and 10.9 g of 3,4-dimethoxyphenethylamine is heated at 130° to 140° C. for 2 hours. After cooling, chloroform is added to the reaction mixture, and said mixture is washed with water. The mixture is dried and evaporated to remove solvent. 30 ml of ethanol are added to the residue obtained. Then, hydrochloric acid-containing diethylether is added to the ethanol mixture, and crystalline precipitates are collected by filtration. 3.0 g of α-(3,4-dimethoxyphenethylaminomethyl)-2-methoxybenzylalcohol hydrochloride are obtained as crystals. M.p. 142°–143° C.

EXAMPLE 3

(1) 1.7 g of 2-methoxy-α-chloroacetophenone are dissolved in 30 ml of dioxane, and 12 ml of water are added thereto. 600 mg of sodium borohydride are added gradually to the solution at 10° to 20° C. Then, the mixture is treated in the same manner as described in Example 2-(1). 1.4 g of α-chloromethyl-2-methoxybenzylalcohol are obtained as a crude oil.

(2) 1.4 g of α-chloromethyl-2-methoxybenzylalcohol (crude oil) are dissolved in 12 ml of dioxane, and a solution of 840 mg of potassium hydroxide in 5 ml of water is added thereto. The mixture is stirred at room temperature for 3 hours. Then, the reaction mixture is poured into ice-water, and the aqueous mixture is extracted with benzene. The extract is dried and evaporated to remove solvent. 0.5 g of 2-(2-methoxyphenyl)oxirane are obtained as a crude product.

(3) A mixture of 0.5 g of 2-(2-methoxyphenyl)oxirane (crude product) and 600 mg of 3,4-dimethoxyphenethylamine is heated at 130° to 140° C. for 2 hours. After cooling, chloroform is added to the reaction mixture, and said mixture is washed with water. The mixture is dried and evaporated to remove solvent. 2 ml of ethanol are added to the residue obtained. Then, hydrochloric acid-containing diethylether is added to the ethanol mixture, and crystalline precipitates are collected by filtration. 290 mg of α-(3,4-dimethoxyphenethylaminomethyl)-2-methoxybenzylalcohol hydrochloride are obtained as crystals. M.p. 142°–143° C.

EXAMPLE 4

(1) A solution of 3.5 g of 2-methoxy-α-chloroacetophenone in 10 ml of methylenechloride is added dropwise to 10.5 g of 3,4-dimethoxyphenethylamine at room temperature. The mixture is refluxed for 1 hour, whereby a solution containing α-(3,4-dimethoxyphenethylamino)-2-methoxyacetophenone is obtained.

(2) 10 ml of ethanol are added to the α-(3,4-dimethoxyphenethylamino)-2-methoxyacetophenone solution obtained in paragraph (1). A solution of 0.9 g of sodium hydroxide in one ml of water is added to the solution under ice-cooling. Then, 1.0 g of sodium borohydride is added gradually to the solution, and the mixture is stirred at the same temperature for 30 minutes and at room temperature for 1.5 hours. The reaction mixture is evaporated to remove solvent. The residue thus obtained is dissolved in chloroform, and the chloroform solution is washed with water. The chloroform solution is dried and evaporated to remove solvent. The oily residue thus obtained is dissolved in 30 ml of ethanol, then diethyl ether containing hydrochloric acid is added to the ethanol mixture and crystalline precipitates are collected by filtration. 3.35 g of α-(3,4-dimethoxyphenethylaminomethyl)-2-methoxybenzylalcohol hydrochloride are obtained. M.p. 142°–143° C.

EXAMPLE 5

90 g of α-(3,4-dimethoxyphenethylaminomethyl)-2-methoxybenzylalcohol (Free Base) are dissolved in 500 ml of ethyl acetate, and 57 g of L-acetylphenylalanine are dissolved therein at about 50° C. The solution is allowed to stand at room temperature for 2 days. Crystalline precipitates are collected by filtration, and the precipitates are recrystallized twice from ethyl acetate. 56 g of l-α-(3,4-dimethoxyphenethylaminomethyl)-2-methoxybenzylalcohol L-acetylphenylalanine salt are obtained. M.p. 123°–125° C. $[\alpha]_D^{25°}$ 0°(C = 1, methanol)

56 g of the salt obtained are dissolved in chloroform, and the solution is washed with an aqueous 10% potassium carbonate solution and water, successively. Then, the solution is dried and evaporated to remove solvent. The crystals thus obtained are recrystallized from ethyl acetate, whereby 25 g of l-α-(3,4-dimethoxyphenethylaminomethyl)-2-methoxybenzylalcohol (Free Base) are obtained. M.p. 103°–104° C. $[\alpha]_D^{25°}$ −44.8°(C = 1, methanol) Hydrochloride: M.p. 144°–145° C. $[\alpha]_D^{25°}$ −58.0°(C = 1, methanol)

EXAMPLE 6

(1) 2 g of 2-ethoxyacetophenone are dissolved in 20 ml of dioxane, and a solution of 2 g of selenium dioxide in one ml of water is added thereto. The solution is refluxed for 10 hours. After the reaction, insoluble materials are removed by filtration, and the filtrate is concentrated. The residue thus obtained is dissolved in ethyl acetate. The ethyl acetate solution is washed with water and then with an aqueous sodium bicarbonate solution and water. Then, said solution is dried and evaporated to remove solvent. 2.1 g of 2-ethoxyphenylglyoxal are obtained as a crude oil.

(2) 2.1 g of 2-ethoxyphenylglyoxal (crude oil) are dissolved in 20 ml of ethanol, and 1.85 g of 3,4-dimethoxyphenethylamine are added thereto. The solution is stirred at room temperature for 30 minutes, whereby a solution containing α-(3,4-dimethoxyphenethylimino)-2-methoxyacetophenone is obtained. 0.6 g of sodium borohydride is added gradually to said solution under ice-cooling, and the mixture is stirred at room temperature for one hour. The reaction mixture is evaporated to remove solvent. Water is added to the thus obtained residue. Then, the aqueous mixture is extracted with chloroform. The extract is washed with water, dried and then evaporated to remove solvent. The oily residue thus obtained is treated with hydrochloric acid and recrystallized from a mixture of isopropanol and ether. 3.1 g of α-(3,4-dimethoxyphenethylaminomethyl)-2-ethoxybenzylalcohol hydrochloride are obtained. M.p. 169°–170° C.

Analysis calculated for $C_{20}H_{27}O_4N.HCl$
C, 62.90; H, 7.39; N, 3.67; Cl, 9.28
Found C, 62.77; H, 7.38; N, 3.94; Cl, 9.51

EXAMPLE 7

2 g of 2-n-butoxyacetophenone and 1.7 g of selenium dioxide are treated in the same manner as described in Example 6-(1). 2 g of 2-n-butoxyphenylglyoxal thus obtained are dissolved in 6 ml of dimethylsulfoxide, and 1.8 g of 3,4-dimethoxyphenethylamine are added thereto. The solution is stirred at room temperature for 30 minutes. Then, 12 ml of ethanol are added to the solution. After ice-cooling, 0.55 g of sodium borohydride is added gradually to the solution, and the mixture is stirred at room temperature for 1 hour. The reaction mixture is evaporated to remove solvent. Water is added to the thus obtained residue, and the aqueous mixture is extracted with ethyl acetate. The extract is washed with water, dried and then evaporated to remove solvent. The oily residue thus obtained is treated with hydrochloric acid and recrystallized from a mixture of ethanol and ether. 2.6 g of α-(3,4-dimethoxyphenethylaminomethyl)-2-n-butoxybenzylalcohol hydrochloride are obtained. M.p. 128°–129° C.

Analysis calculated for $C_{22}H_{31}O_4N.HCl$
C, 64.45; H, 7.87; N, 3.42; Cl, 8.65
Found C, 64.38; H, 7.82; N, 3.47; Cl, 8.40

What we claim is:

1. A compound of the formula:

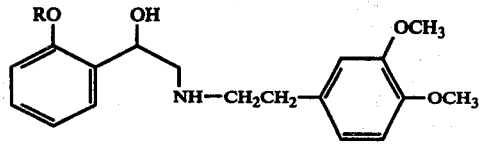

wherein R is a lower alkyl group having 1–4 carbon atoms, or a pharmaceutically acceptable acid addition salt thereof.

2. The compound of claim 1, wherein said compound is an optically active l-enantiomer.

3. The compound of claim 1, wherein R is methyl.

4. The compound of claim 3, wherein said compound is an optically active l-enantiomer.

5. A pharmaceutical composition consisting essentially of a pharmaceutically acceptable excipient and the compound of claim 1, said composition capable of providing a decrease in blood sugar when administered to a warm blooded animal.

6. A pharmaceutical composition consisting essentially of a pharmaceutically acceptable excipient and the compound of claim 3, said composition capable of providing a decrease in blood sugar when adminstered to a warm blooded animal.

7. The composition of claim 5 suitable for administration to a warm blooded animal providing for a dosage of said compound between 5 μg and 10 mg per kilogram of body weight per day.

8. The composition of claim 5 suitable for administration to a warm blooded animal providing for a dosage of said compound between 20 μg and 2 mg per kilogram of body weight per day.

UNITED STATES PATENT OFFICE
CERTIFICATE OF CORRECTION

PATENT NO. : 4,131,686
DATED : December 26, 1978
INVENTOR(S) : MUNEYOSHI IKEZAKI, et al It is certified that error appears in the above-identified patent and that said Letters Patent are hereby corrected as shown below:

Item [75] Inventors: line 1, cancel "Yashushi" insert

-- Yasushi --

Signed and Sealed this

Third Day of April 1979

[SEAL]

Attest:

RUTH C. MASON
Attesting Officer

DONALD W. BANNER
Commissioner of Patents and Trademarks